United States Patent [19]

Bourguinat

[11] Patent Number: 5,548,400

[45] Date of Patent: Aug. 20, 1996

[54] METHOD AND APPARATUS FOR INSPECTING HONEYCOMB STRUCTURES USING OPTICAL FIBRES

[75] Inventor: Jean C. M. Bourguinat, Meudon, France

[73] Assignee: Sochata, Velizy Villacoublay, France

[21] Appl. No.: 389,643

[22] Filed: Feb. 16, 1995

[30] Foreign Application Priority Data

Feb. 16, 1994 [FR] France .................................. 94 01734

[51] Int. Cl.⁶ .................................................. G01N 21/88
[52] U.S. Cl. .......................................... 356/237; 356/241
[58] Field of Search ..................................... 356/237, 239, 356/241

[56] References Cited

U.S. PATENT DOCUMENTS

| | | | |
|---|---|---|---|
| 4,319,840 | 3/1982 | Kondo et al. | 356/241 |
| 4,560,273 | 12/1985 | Ando et al. | 356/241 |
| 4,766,325 | 8/1988 | Merkenschlager et al. | 356/241 |
| 5,078,005 | 1/1992 | Krempel et al. | 73/73 |
| 5,463,462 | 10/1995 | Ohnishi et al. | 356/237 |

FOREIGN PATENT DOCUMENTS

| | | |
|---|---|---|
| 0448894A1 | 10/1991 | European Pat. Off. . |
| 2913918 | 10/1980 | Germany . |
| 59-20840 | 2/1984 | Japan ...................................... 356/237 |

Primary Examiner—Richard A. Rosenberger
Attorney, Agent, or Firm—Oblon, Spivak, McClelland, Maier & Neustadt, P.C.

[57] ABSTRACT

The connection between a support and a honeycomb structure defining a network of parallel cells is inspected by transmitting a beam of light into a first cell of the honeycomb structure by an optical fiber, termed an illuminating fiber, which is connected at one end to a light emitter, and simultaneously detecting any light which leaks from the first cell into an adjacent cell by an optical fiber, termed an observation fiber, which is connected to a converter converting light into an electrical signal.

22 Claims, 3 Drawing Sheets

METHOD AND APPARATUS FOR INSPECTING HONEYCOMB STRUCTURES USING OPTICAL FIBRES

BACKGROUND OF THE INVENTION

1. Field of the Invention

The invention relates to a method of inspecting the connection between a support and an alveolar structure, such as those called honeycomb structures, and to an apparatus for use in carrying out the method.

As used herein, the term honeycomb structure includes any kind of alveolar structure defining a network of parallel cells, whatever the geometry of the cells may be, and the term bonding is intended to cover any method of forming the connection between the honeycomb structure and the support, whether by glueing, welding, brazing or any other suitable means.

Because of their lightness and compression strength, the aeronautical industry is making ever-increasing use of honeycomb structures as structural reinforcement, for example, in turbomachine casings and aircraft floors. For example, it is known to place an annular band of honeycomb material on the outside of the fan casing of a turbojet engine near the fan blades as a replacement for the reinforcing ribs which were previously used and the machining of which meant that the unfinished article had to have a considerable overthickness with respect to the finished article.

This honeycomb structure is a very effective strengthening structure provided that it is bonded at the base of all of its cells to the part which is to be strengthened. To ensure that this is so, a very thorough statistical inspection of the connection must be made. If there is a fault resulting, for example, from a lack of brazing, this will manifest itself as a passage between two adjacent cells.

2. Discussion of the Prior Art

Various methods of making these inspections are known.

In a first method an operator makes an endoscopic inspection of the cell bases by brightly illuminating a cell and examining the base of the adjacent cell to see if a bonding fault allows a ray of light to pass between the illuminated cell and the adjacent cell. This check is made statistically by inspecting the honeycomb band at three or four places over its width and every five centimeters along its length. Consequently, inspecting a 15 cm wide honeycomb band bonded as a reinforcement on a fan casing of 183 cm diameter may take more than eight hours, resulting in severe visual fatigue of the operator and, therefore, a decreasing reliability of the inspection with time.

In a second method, called the capillary method, the honeycomb structure is dipped into a very wetting fluorescent liquid. The liquid is retained by capillary action in cells where the honeycomb and its bonding are free from defects, but faulty cells do not retain the liquid.

However, this method has many problems. Firstly, the liquid contains compounds, such as trichloroethane, which are dangerous to the operator since they are flammable, volatile and toxic, and hence contact with their vapors must be carefully avoided. Another disadvantage is that inspecting a casing entails dipping it into a tank to wet it, so that bulky installations are necessary. Finally, the inspection operation itself takes as long as the endoscopic inspection operation mentioned earlier.

In a third method described in EP-A-0448894 an enclosure supplied with compressed air is applied to a first zone of the honeycomb structure to be inspected, and a check is made as to whether the air can escape from the inspected zone due to bonding faults. The absence or presence of such faults can readily be confirmed by measuring the leakage discharge.

While this method is satisfactory for fairly large honeycomb structures having a cell size of at least 4 mm, it is more difficult, although not impossible, to use with smaller honeycombs. Nowadays, however, honeycomb structures having a cell size of approximately 2 mm are common. Also, this method is noisy.

Furthermore, using this method does not directly provide an accurate result. In a first phase a first measurement must be made to establish the approximate site of possible defects, after which a fine search must be carried out to locate the defects or to inspect areas which are difficult to access using a variant of the method specifically adapted to localized inspection of small areas.

This method is therefore relatively inconvenient to use.

SUMMARY OF THE INVENTION

With a view to avoiding these problems, according to a first aspect of the invention there is provided a method of inspecting the connection between a support and a honeycomb structure defining a network of parallel cells, including the steps of:

introducing one end of a first optical fiber, referred to as an illuminating fiber, into a first cell of said honeycomb structure, said illuminating fiber being connected at its other end to light emission means;

introducing one end of at least one second optical fiber, referred to as an observation fiber, into at least one cell of said honeycomb structure adjacent said first cell, said observation fiber being connected at its other end to detection means for converting light into an electrical signal;

transmitting a beam of light from said light emission means through said illuminating fiber to illuminate said first cell; and, synchronously detecting any light which leaks from said illuminated first cell into said at least one adjacent cell containing said at least one observation fiber and which is transmitted by said observation fiber to said detection means connected thereto.

This method is an improvement over the prior art methods because the operator's task is greatly facilitated, no harmful or flammable product has to be used, and the method is accurate and can readily be automated and/or computerized.

According to a further aspect of the invention, there is provided a method of inspecting the connection between a support and a honeycomb structure defining a network of parallel cells, including the steps of:

positioning one end of a first optical fiber, referred to as an illuminating fiber, in proximity to the entrance to a first cell of said honeycomb structure, said illuminating fiber being connected at its other end to light emission means;

positioning one end of at least one second optical fiber, referred to as an observation fiber, in proximity to the entrance to at least one cell of said honeycomb structure adjacent said first cell, said observation fiber being connected at its other end to detection means for converting light into an electrical signal;

transmitting a beam of light from said light emission means through said illuminating fiber to illuminate said first cell; and, synchronously detecting any light which leaks from said illuminated first cell into said at least one adjacent cell and which is received and transmitted by said observation fiber to said detection means connected thereto.

As will be appreciated this second aspect of the invention has the same advantages as the first over the prior art.

The invention also provides an apparatus for use in carrying out the inspection methods of the invention, the apparatus comprising an optical fiber holder, at least two optical fibers extending through and supported by said holder, light emission means connected to one end of at least one of said optical fibers, detection means for converting light into an electrical signal connected to one end of each of said optical fibers not connected to said light emission means, said one ends of said optical fibers connected to said light emission means and said detection means being disposed on the same side of said holder as each other.

The free other ends of the optical fibers may project beyond the holder, on the side thereof opposite the side on which the ends connected to the light-emission means and the detection means are disposed, by a distance less than the depth of the cells to be inspected.

Alternatively the free other ends of the optical fibers may be flush with the surface of the holder on the side thereof opposite the side on which the said one ends are disposed.

The apparatus in accordance with the invention has the advantage of simplicity compared with the prior art, and can be associated with means for automating the inspection.

The honeycomb structure can be inspected by sampling without the need to inspect all the cells, and a microcomputer can be used to select the zones to be inspected and to analyse the results by using statistical control techniques.

Further features and advantages of the invention will become more apparent from the following description of the preferred embodiments, given by way of example only, with reference to the accompanying drawings.

DESCRIPTION OF THE PREFERRED EMBODIMENTS

Figure 1:
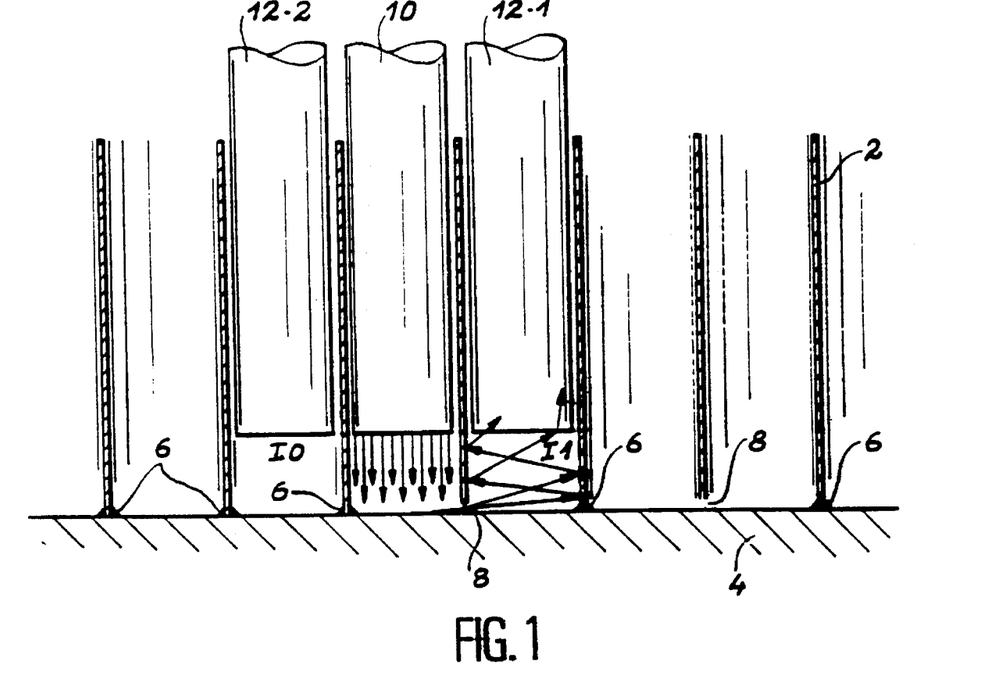
FIG. 1 is a diagrammatic sectional view of part of a honeycomb structure bonded to a support and showing the principles of a first embodiment of a method of inspection in accordance with the invention.

Referring to FIG. 1 there can be seen a honeycomb structure 2 consisting of a network of parallel cells, a support 4, and a connection 6 between the structure 2 and the support 4. The connection 6 may be formed by glueing, brazing, or welding. The aim of the method in accordance with the invention is to detect faults, such as shown at 8, in the connection 6. To this end, in this embodiment an optical fiber 10, termed an illuminating fiber, having one end connected to a light emitter, such as a diode (not shown in FIG. 1), has its free other end introduced into a cell of the honeycomb structure 2. An optical fiber 12-1, termed an observation fiber, connected at one end to means for converting light into an electrical signal, such as a photodiode (not shown in FIG. 1), has its free other end introduced, for example, in a direction parallel to the illuminating fiber 10, into a cell adjacent the first cell containing the fiber 10. If the cell receiving the illuminating fiber 10 has n immediately adjacent cells in the honeycomb structure, up to n observation fibers 12-1, 12-2, . . . , 12-n can be used at the same time, each being introduced into a respective one of the adjacent cells. In FIG. 1, two such observation cells 12-1 and 12-2 are shown.

By means of the light emitter which is connected to the illuminating fiber 10 and which may take the form, for example, of a infrared-emitting diode, a light beam is transmitted into the cell containing the illuminating fiber. If there is no gap in the connection between the honeycomb structure and the support at the base of this cell, each observation fiber in the adjacent cells will produce a signal corresponding to a certain light intensity $I_0$. In the case shown in FIG. 1, where there is a gap 8 in the connection at the base of the cell containing the illuminating fiber 10 and the adjacent cell containing the observation fiber 12-1, this observation fiber will transmit light which has leaked into its cell from the illuminated cell through the gap 8 to its detector to produce a signal corresponding to an illumination intensity $I_1$ greater than the intensity $I_0$ measured when there is no gap.

The measured signal can be analysed by an appropriate processing unit to provide a diagnosis of the state of the connection between the honecomb structure and the support.

This measurement can be repeated by moving the assembly comprising the illuminating fiber 10 and the observation fibers (12-1, 12-2, . . . ) into different cells of the honeycomb, and an accurate picture of the state of the connection can be obtained in this way.

Figure 2:
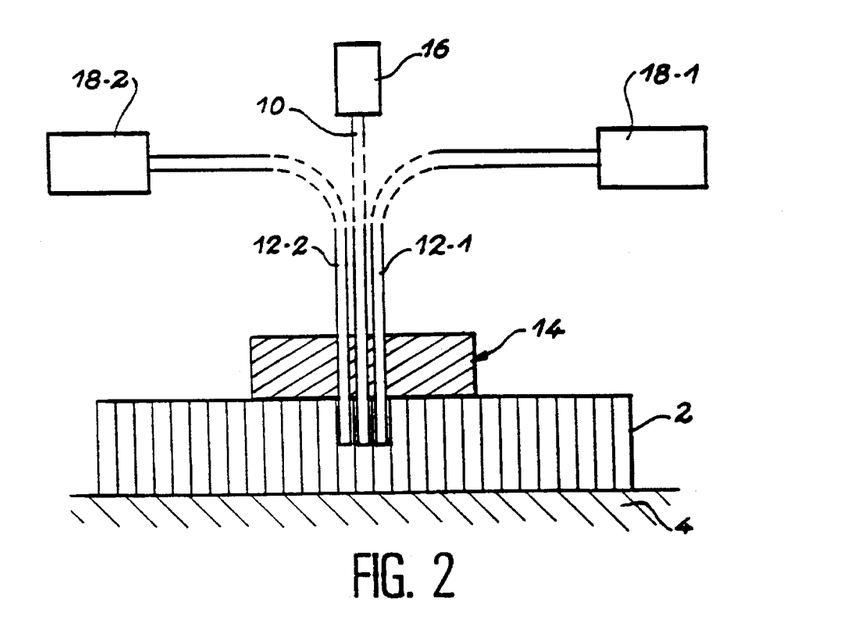
FIG. 2 is a diagrammatic view of an apparatus for use in the first embodiment.

An apparatus for use in this first embodiment is shown in FIG. 2, and comprises an optical fiber holder 14 through which at least two optical fibers extend, namely a fiber 10 for illuminating a cell and at least one fiber 12-1, 12-2 for observation in an adjacent cell. If the geometric structure of the honeycomb is such that each cell is surrounded by n immediately adjacent cells, the illuminating fiber 10 may be surrounded by any number of observation fibers between 1 and n (12-1, 12-2, . . . , 12-n). The illuminating fiber 10, is connected at one end to a light emitter 16, such as an electroluminescent diode, which emits infrared light. Each observation fiber is connected to a detector (18-1, 18-2, . . .), such as a photodiode, for converting light into an electrical signal. The light emitter 16 and the detectors (18-1, 18-2, . . . ) are both disposed on the same side of the holder as each other, whereas on the other side thereof the free ends of the fibers extend beyond the holder by a distance h which is not necessarily the same for all the fibers but is less than the depth p of the cells of the honeycomb.

To make an inspection the holder 14 is placed on the honeycomb 2 with the fibers projecting into a group of adjacent cells, and light is then transmitted through the illuminating fiber 10 to one of the cells while at the same time the intensity of light in the cells adjacent thereto is measured to determine the presence or absence of a fault 8 in the connection 6 between the honeycomb 2 and the support 4 at the base of the cells. The holder 14 and the optical fibers are then shifted to another group of cells to continue checking for faults in the bonding. The shift can be made either manually, or automatically such as with the aid of means to be described hereinafter. Also, means (not shown in FIG. 2) may be provided to retain the fibers in a fixed position relative to the holder 14, this means also enabling the distance h to be adjusted.

Figure 3:
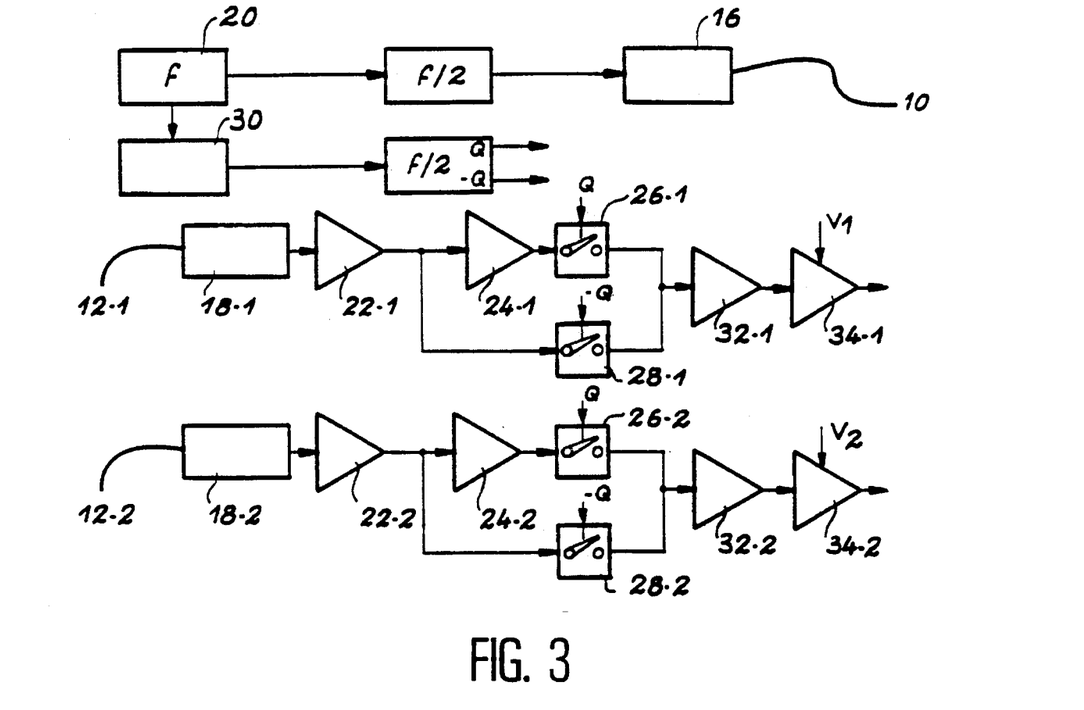
FIG. 3 is a block circuit diagram of an electronic control and detection analysis circuit for an apparatus in accordance with the invention.

The general principle of an electronic control and measurement circuit for use with the apparatus is shown in FIG. 3 in the case where the apparatus has two observation fibers.

The light emitter 16, for example an infrared diode, is on-off modulated by an oscillator at a frequency f/2. The illuminating fiber 10 is directly connected to the light emitter 16 and hence transmits light modulated, for example, in square wave form.

The detectors (18-1, 18-2, ... ), for example photodiodes, convert the detected light into an electrical signal output, for each observation fiber (12-1, 12-2, ... ), a current proportional to the light flux reaching them. This current is converted to a voltage by a current-to-voltage converter (22-1, 22-2, ... ) which outputs, for example, 10 V/nA. This voltage is supplied both to a switch (28-1, 28-2, ... ) and to an amplifier (24-1, 24-2, ... ) which inverts the voltage and delivers it to a switch (26-1, 26-2, ... ). The switches (26-1, 26-2, ... ; 28-1, 28-2, ... ) are controlled by a delayed local oscillator 30 which is in turn piloted by the oscillator 20, so that the input of a low pass filter (32-1, 32-2, ... ) receives either the direct voltage, when the diode is illuminated, or the inverted voltage, when the diode is extinguished.

The low pass filter averages the signal, and thus suppresses the DC background of the detected signal and any disturbances introduced by ambient lighting modulated at 50 or 100 hertz and all the interference correctly sampled at the oscillator frequency- The low pass filter outputs to a comparator (34-1, 34-2, ... ) which compares the filter output with a reference value ($V_1$, $V_2$, ... ) and which activates an electroluminescent diode if the comparison indicates the presence of a fault 8. The reference value ($V_1$, $V_2$, ... ) of the comparator, and hence the detection sensitivity of the circuit, is adjustable by a potentiometer. The comparator output can also be connected to means for memorizing the result of the comparison and/or means for displaying these results, for example in graphic or cartographic form.

Such a measurement circuit chain is provided for each observation fiber, so if there are n observation fibers, there will be n identical electronic circuit chains.

In a second embodiment of the method in accordance with invention, the inspection is carried out in the same way as in the first embodiment except that the fibers do not project into the cells but are positioned flush with the entrances thereof. In a first phase, therefore, the free end of an optical fiber connected to a light emitter, such as an electroluminescent infrared diode, is positioned at the entrance of a first cell, and the free end of at least one optical fiber connected at its other end to a detector for converting light into an electrical signal is positioned at the entrance of at least one cell adjacent the first cell. This second embodiment has the advantage over the first embodiment of not needing the optical fibers to be introduced into the cells. In other respects, such as light emission and synchronous detection, the first and second embodiments are identical.

Figure 4:
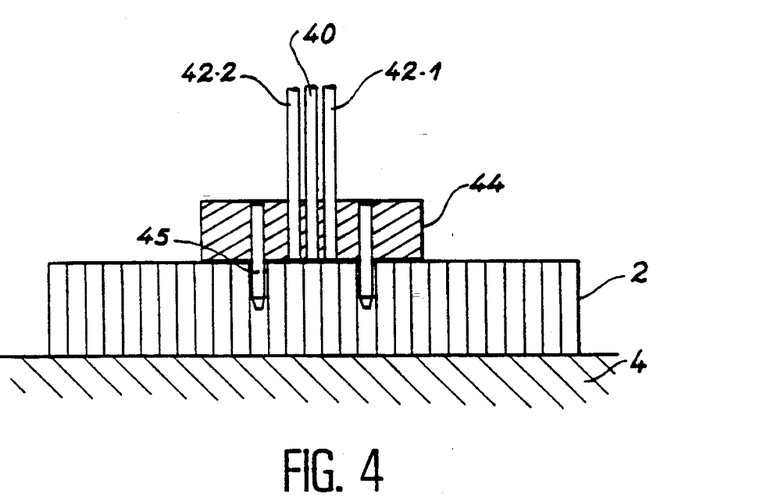
FIG. 4 is a view similar to FIG. 2, but showing part of an apparatus for use in carrying out a second embodiment of the method in accordance with the invention.

An apparatus for use in the second embodiment is shown in FIG. 4, and comprises a holder 44 for supporting optical fibers (an illuminating fiber 40 and observation fibers 42-1, 42-2) in such manner that the free end of each fiber is flush with the holder surface. Also, the holder 44 has centering pins 45 to locate and stabilize the holder and optical fiber system during an inspection phase, and means (not shown) for adjusting the position of the fibers and retaining them in a predetermined position. In operation, the pins are received in cells adjacent the cells which are being inspected. Although not shown in FIG. 4, a light emitter is connected to the illuminating fiber 40 and detectors for converting light into an electrical signal are connected to the observation fibers 42-1, 42-2, ... as in the apparatus shown in FIG. 2 for use in the first embodiment, and the electronic measurement circuit used with the apparatus is the same as hereinbefore described with reference to FIG. 3.

Once all the measurement operations have been performed in a group of cells the holder 44 with the fibers attached thereto is raised so as to disengage the centering pins from the honeycomb and the holder is moved to a different measuring position on the honeycomb surface. This movement can be made either manually or automatically as described below.

Figure 5:
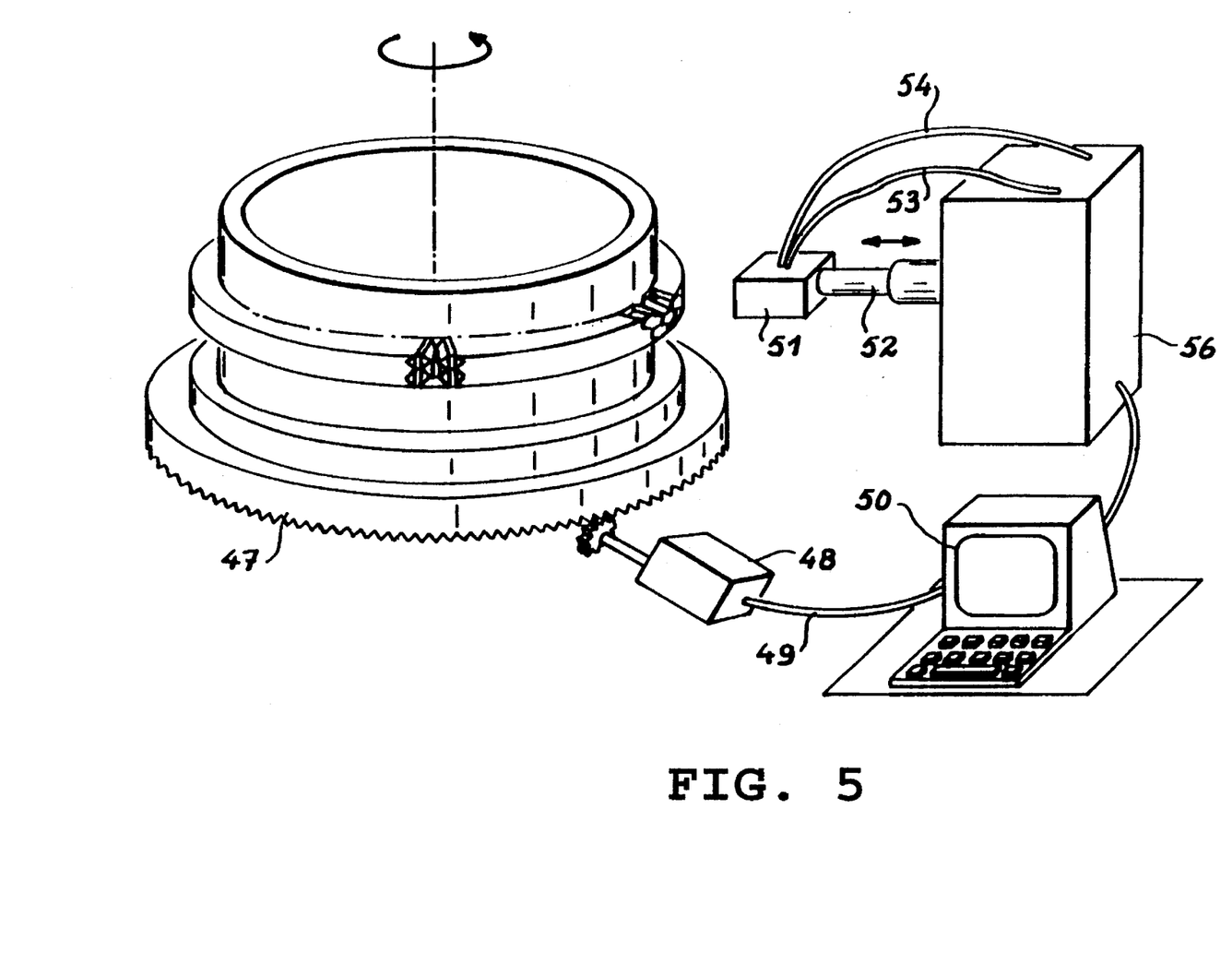
FIG. 5 is a diagrammatic view of an automated arrangement for carrying out a method of inspection in accordance with the invention.

FIG. 5 shows how an apparatus in accordance with the invention can be automated to inspect a honeycomb band applied to the outside of a turbojet engine fan casing.

The article to be inspected is placed on a turntable 47 having a mechanism 48 for rotating it sequentially, and this mechanism 48 has an output 49 connected to a recording unit, such as a microprocessor 50, for recording the angular position coding of the article.

A box 51 incorporates one of the measuring units described earlier—i.e., a holder (not shown) in which an optical illuminating fiber and one or more optical observation fibers are secured such that their free ends either extend beyond the holder surface which is arranged to contact the honeycomb to be inspected (first embodiment of the invention) or are flush with the said holder surface (second embodiment of the invention).

The box 51 is carried by a support arm 52 which is disposed radially of the article and is movable horizontally or vertically in one, two or three spatial dimensions. This movement is piloted by a control unit and/or by an operator by way of the microcomputer 50 so as to place the holder against the honeycomb to be inspected at the required place.

In FIG. 5 there can be seen an illuminating fiber 53 and an observation fiber 54, although it will be appreciated that there may be more than one observation fiber. The optical means (emitting diode and detecting photodiodes) and electronic means associated with the fibers 53 and 54 are housed in a cabinet 56 which also houses the mechanism controlling the movement of the arm 52.

The performance of the complete inspection operation can be controlled by the microcomputer 50, which may also comprise means for storing measured data and spatial data concerning the positioning of the arm and the angular position of the turntable, means for comparing the measured data for the light intensity received and transmitted by each observation fibre with calibrated data, means for inferring from the comparisons the presence or absence of faults in the connection between the honeycomb and the support, and means, such as a screen, for displaying a map of the honeycomb under inspection and for indicating the detected faults.

Obviously, numerous modifications and variations of the present invention are possible in light of the above teachings. It is therefore to be understood that within the scope of the appended claims, the invention may be practiced otherwise than as specifically described herein.

I claim:

1. A method of inspecting the connection between a support and a honeycomb structure defining a network of parallel cells, including the steps of:

introducing one end of a first optical fiber, said fiber comprising an illuminating fiber, into a first cell of said cells of said honeycomb structure, connecting said illuminating fiber at its other end to light emission means;

introducing one end of at least one second optical fiber, said second optical fiber comprising an observation fiber, into at lest one cell of said honeycomb structure adjacent said first cell, connecting said observation fiber at its other end to detection means for converting light into an electrical signal;

transmitting a beam of on-off modulated light from said light emission means through said illuminating fiber to illuminate said first cell; and, synchronously detecting and DC background suppressing any light which leaks from said illuminated first cell into said at least one adjacent cell containing said at least one observation fiber and which is transmitted by said observation fiber to said detection means connected thereto.

2. A method according to claim 1, wherein said light emission means comprises an infrared light emitting diode.

3. A method according to claim 1, wherein said detection means comprises a respective photodiode for each said observation fiber.

4. A method of inspecting the connection between a support and a honeycomb structure defining a network of parallel cells, including the steps of:

positioning one end of a first optical fiber, said fiber comprising an illuminating fiber, in proximity to the entrance to a first cell of said honeycomb structure, connecting said illuminating fiber at its other end to light emission means;

positioning one end of at least one second optical fiber, said second fiber comprising an observation fiber, in proximity to the entrance to at least one cell of said honeycomb structure adjacent said first cell, connecting said observation fiber at its other end to detection means for converting light into an electrical signal;

transmitting a beam of on-off modulated light from said light emission means through said illuminating fiber to illuminate said first cell; and synchronously detecting and DC background suppressing any light which leaks from said illuminated first cell into said at least one adjacent cell and which is received and transmitted by said observation fiber to said detection means connected thereto.

5. A method according to claim 4, wherein said light emission means comprises an infrared light emitting diode.

6. A method according to claim 4, wherein said detection means comprises a respective photodiode for each of said observation fibers.

7. Apparatus for use in inspecting the connection between a support and a honeycomb structure defining a network of parallel cells, comprising:

an optical fiber holder, at least two optical fibers extending through and being supported by said holder, light on-off modulated emission means connected to one end of at least one of said optical fibers, detection means for converting light into an electrical signal and suppressing DC background, said detection means being connected at one end of each of said optical fibers not connected to said light emission means, said one end of each of said optical fibers being connected to said light emission means and said detection means being disposed on the same side of said holder.

8. Apparatus according to claim 7, wherein the free other ends of said optical fibers project beyond said holder, on the side thereof opposite that on which said one ends of said fibers are disposed, by a distance less than the depth of said cells of said honeycomb structure.

9. Apparatus according to claim 7, wherein the free other ends of said optical fibers are flush with the surface of said holder on the side thereof opposite that on which said one ends of said fibers are disposed.

10. Apparatus according to claim 9, wherein said holder comprises pins for engaging in cells of said honeycomb structure to locate said holder and said free ends of said optical fibers relative to the cells to be inspected.

11. Apparatus according to claim 7, which comprises means for moving said holder relative to said honeycomb structure to be inspected.

12. A method of inspecting the connection between a support and a honeycomb structure defining a network of parallel cells, including the steps of:

introducing one end of a first optical fiber, said fiber comprising an illuminating fiber, into a first cell of said cells of said honeycomb structure, connecting said illuminating fiber at its other end to a light emitter;

introducing one end of at least one second optical fiber, said second optical fiber comprising an observation fiber, into at least one cell of said honeycomb structure adjacent said first cell;

connecting said observation fiber at its other end to a detector converting light into an electrical signal;

transmitting a beam of on-off modulated light from said light emitter through said illuminating fiber and illuminating said first cell; and synchronously detecting an DC background suppressing any light which leaks from said illuminated first cell into said at least one adjacent cell containing said at least one observation fiber and which is transmitted by said observation fiber to said detector connected thereto.

13. A method according to claim 12, wherein said light emitter comprises an infrared light emitting diode.

14. A method according to claim 12, wherein said detector comprises a respective diode for each of said observation fibers.

15. A method of inspecting the connection between a support and a honeycomb structure defining a network of parallel cells, including the steps of:

positioning one end of a first optical fiber, said optical fiber comprising an illuminating fiber, in proximity to the entrance of a first cell of said honeycomb structure;

connecting said illuminating fiber at its other end to a light emitter;

positioning one end of at least one second optical fiber, said second optical fiber comprising an observation fiber, in proximity to the entrance to at least one cell of said honeycomb structure adjacent said first cell;

connecting said observation fiber at its other end to a detector converting light into an electrical signal;

transmitting a beam of on-off modulated light from said light emitter through said illuminating fiber and illuminating said first cell; and synchronously detecting and DC background suppressing any light which leaks from said illuminated first cell into said at least one adjacent cell and which is received and transmitted by said observation fiber to said detector connected thereto.

16. A method according to claim 15, wherein said light emitter comprises an infrared light emitting diode.

17. A method according to claim 15, wherein said detector comprises a respective photodiode for each of said observation fibers.

18. An apparatus for use in inspecting the connection between a support and a honeycomb structure defining a network of parallel cells, comprising:

an optical fiber holder, at least two optical fibers extending through and being supported by said holder;

an on-off modulated light emitter connected to one end of at least one of said optical fibers;

a detector converting light into an electrical signal and suppressing DC background, said detector being connected at one end of each of said optical fibers not connected to said light emitter, said one ends of said optical fibers connected to said light emitter and said detector being disposed on the same side of said holder.

19. Apparatus according to claim 18, wherein the free other ends of said optical fibers project beyond said holder, on the side thereof opposite that on which said one ends of said fibers are disposed, by distance less than the depth of said cells of said honeycomb structure.

20. Apparatus according to claim 18, wherein the free other ends of said optical fibers are flush with the surface of said holder on the side thereof opposite that on which said one ends of said fibers are disposed.

21. Apparatus according to claim 20, wherein said holder comprises pins engaging in cells of said honeycomb structure and locating said holder and said free ends of said optical fibers relative to the cells to be inspected.

22. Apparatus according to claim 18, which comprises a mechanism moving said holder relative to said honeycomb structure to be inspected.

* * * * *

UNITED STATES PATENT AND TRADEMARK OFFICE
CERTIFICATE OF CORRECTION

PATENT NO. : 5,548,400
DATED : August 20, 1996
INVENTOR(S) : Bourguinat

It is certified that error appears in the above-indentified patent and that said Letters Patent is hereby corrected as shown below:

Column 4, lines 8 and 9, change "n" to --$\underline{n}$--;

line 32, change "honecomb" to --honeycomb--;

line 44, change "by n" to --by $\underline{n}$--;

line 47, change "n" to --$\underline{n}$--;

line 55, change "h" to --$\underline{h}$--;

line 57, change "p" to --$\underline{p}$--;.

Column 5, line 5, change "h" to --$\underline{h}$--;

line 32, change "oscillator frequency-" to --oscillator frequency.-- line 43, change "n" to --$\underline{n}$--;

line 44, change "n" to --$\underline{n}$--.

UNITED STATES PATENT AND TRADEMARK OFFICE
CERTIFICATE OF CORRECTION

PATENT NO. : 5,548,400
DATED : August 20, 1996
INVENTOR(S) : Bourguinat

It is certified that error appears in the above-indentified patent and that said Letters Patent is hereby corrected as shown below:

Column 6, line 53, change "fibre" to --fiber--.

Signed and Sealed this

Third Day of June, 1997

Attest:

BRUCE LEHMAN

Attesting Officer     Commissioner of Patents and Trademarks